United States Patent [19]

Napier et al.

[11] Patent Number: 4,873,241

[45] Date of Patent: Oct. 10, 1989

[54] 2-AMINO-N-(2-PHENYLINDAN-2-YL)ACETAMIDES USEFUL AS ANTI-EPILEPTICS

[75] Inventors: James J. Napier, Chili; Ronald C. Griffith, Pittsford, both of N.Y.

[73] Assignee: Fisons Corporation, Rochester, N.Y.

[21] Appl. No.: 265,087

[22] Filed: Oct. 31, 1988

[51] Int. Cl.$^4$ .................. C07D 295/14; A61K 31/535
[52] U.S. Cl. ......................... 514/237.8; 514/319; 514/423; 514/428; 514/624; 514/626; 544/165; 546/205; 548/537; 548/568; 564/190; 564/194
[58] Field of Search ................. 564/190, 194, 47; 548/568, 537; 546/205; 544/165; 549/467, 469; 514/237.8, 319, 423, 428, 595, 624, 626

[56] References Cited

U.S. PATENT DOCUMENTS

| 3,408,389 | 10/1968 | Bernstein et al. | 540/575 X |
| 3,923,813 | 12/1975 | Vanhoof et al. | 564/194 X |
| 3,923,815 | 12/1975 | Vanhoof et al. | 564/194 X |
| 3,923,887 | 12/1975 | Vanhoof et al. | 564/194 X |
| 4,304,785 | 12/1981 | Griengl et al. | 549/469 X |
| 4,602,035 | 7/1986 | Tegeler et al. | 549/467 X |

FOREIGN PATENT DOCUMENTS 667486 7/1965 Belgium .
0108775 6/1984 Japan .

OTHER PUBLICATIONS

Dai-Ho et al., *Tet. Lett.* 26, 5867-70 (1985).
Sofroniev et al., *Dokl. Bolg. Akad. Nauk.*, 34, 1269-72 (1981).
Minchev et al., *Dokl. Bolg. Akad. Nauk.*, 34, 1111-14 (1981).
Chem. Abstract 64:19517c, abstracting Netherlands Patent Application 6,509,640.
Alesiev et al., *J. Prak. Chem.*, 316, 140-6 (1974).
Minchev et al., *Symp. Pap.-IUPAC Int. Sump. Chem. Nat. Products*, 11th, 3, 174-7 (1978).
Heymans et al., *J. Med. Chem.*, 23, 184-193 (1980).

Primary Examiner—Richard A. Schwartz
Assistant Examiner—E. B. Magrab
Attorney, Agent, or Firm—Seidel, Gonda, Lavorgna & Monaco

[57] ABSTRACT

2-Amino-N-(2-phenylindan-2-yl)acetamides of the following formula are provided

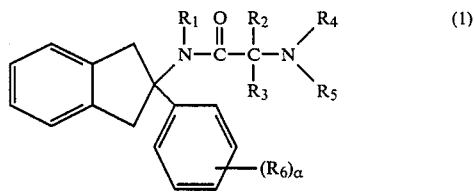

wherein,
a=0 to 3,
$R_1$, $R_2$ and $R_3$ are independently selected from hydrogen and methyl,
$R_4$ is hydrogen or $C_1$-$C_4$ alkyl,
$R_5$ is selected from hydrogen, $C_1$-$C_4$ alkyl, cyclopropyl and (aminomethyl)carbonyl, or
$R_4$ and $R_5$ taken together with the nitrogen atom to which they are attached from a heterocyclic ring selected from pyrrolidinyl, piperidinyl and morpholinyl, or
$R_3$ and $R_4$ taken together with the carbon atom and nitrogen atom to which they are respectively attached form a heterocyclic ring selected from pyrrolidinyl and piperidinyl, and
$R_6$ is selected from hydrogen, halogen, $C_1$-$C_4$ alkoxy, trifluoromethyl, $C_1$-$C_4$ alkyl and combinations thereof.

The compounds have antiepileptic or antihypoxia activity.

21 Claims, No Drawings

2-AMINO-N-(2-PHENYLINDAN-2-YL)ACETA- MIDES USEFUL AS ANTI-EPILEPTICS

BACKGROUND OF THE INVENTION

The invention pertains to substituted 2-amino-N-(2-phenylindan-2-yl)acetamides compounds which are useful as antiepileptic or antihypoxia agents.

The local anesthetic lidocaine is an example of a 2-aminoacetamide with anticonvulsant properties. However it has a short duration of action and has a low oral potency compared to the standard anticonvulsant agents phenobarbital and diphenyl hydantoin (E. I. Isaacson, J. N. Delgado in: *Burger's Medicinal Chemistry*, 4th ed., Part III; M. E. Wolff, Ed.: Wiley Interscience, New York, pp. 850-851 (1981)).

The amine (i) has been obtained as the product of a photochemical rearrangement (G. Dai-Ho, A. J. M. Lan, P. S. Marino, *Tet. Lett.*, 26, 5867–70 (1985).

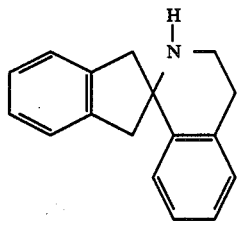
(i)

The following disclose the amine (ii) or aminoacetamide (iii) which are claimed to have anticoagulation activity or to stimulate the succinatoxidase activity of native liver mitochondria in : in vitro experiments. (1) N. Sofroniev, S. Minchev, B. Aleksiev, V. Mikhailow, *Dokl. Bolg. Akad. Nauk.*, 34. 1269–72 (1981); (2) S. Minchev, N. Sofroniev, B. Aleksiev, *Dokl. Bolg. Akad. Nauk.*, 34, 1111–14 (1981); (3) B. Aleksiev, S. Minchev, *J. Prak. Chem.*, 316, 140–6 (1974); (4) S. Minchev, N. Sofroniev, B. Aleksiev, *Symp Pap.-IUPAC Int. Symo Chem. Nat. Products*, 11*th*, 3, 174–7 (1978).

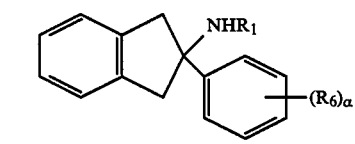
(ii)

(iii)

Compounds of formula (iv) are disclosed in Belgian patent No. 667,486 (1966) where R may be, inter alia. hydrogen; $R_1$ and $R_2$ can be inter alia, methyl or phenyl and B is a basic group containing nitrogen. The compounds are claimed to have analgesic, local anesthetic and CNS-depressant activity.

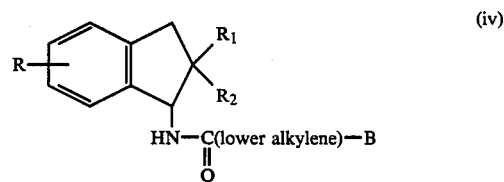
(iv)

SUMMARY OF THE INVENTION

In accordance with the invention there are provided compounds of the formula (1):

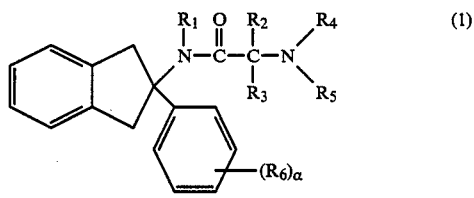
(1)

and pharmaceutically acceptable acid addition salts thereof, including such compounds and salts thereof in the form of their enantiomers, or mixtures of their enantiomers, a=0 to 3, $R_1$, $R_2$ and $R_3$ are independently selected from hydrogen and methyl, $R_4$ is hydrogen or $C_1$-$C_4$ alkyl, $R_5$ is selected from hydrogen, $C_1$-$C_4$ alkyl, cyclopropyl and (aminomethyl)carbonyl, or $R_4$ and $R_5$ taken together with the nitrogen atom to which they are attached from a heterocyclic ring selected from pyrrolidinyl, piperidinyl and morpholinyl, or $R_3$ and $R_4$ taken together with the carbon atom and nitrogen atom to which they are respectively attached form a heterocyclic ring selected from pyrrolidinyl and piperidinyl, and $R_6$ is selected from hydrogen, halogen, $C_1$-$C_4$ alkoxy, trifluoromethyl, $C_1$-$C_4$ alkyl and combinations thereof.

Compounds of this invention possess useful pharmaceutical properties. In particular they possess antiepileptic or antihypoxia activity. Especially useful are those compounds in which $R_1$, $R_2$, $R_3$, $R_4$ and $R_6$ are hydrogen and $R_5$ is hydrogen or (aminomethyl)carbonyl.

Compounds wherein $R_2$ and $R_3$ differ are optically active. The invention relates to racemic and optically resolved forms of such compounds. The invention also relates to pharmaceutically acceptable acid addition salts of the compounds of formula 1.

A method of treating a warm-blooded animal for epilepsy is provided, which method comprises administering to such animal an effective amount of a compound of formula The invention also relates to intermediates of the formula (2):

(2)

wherein $R_1$, $R_6$ and a are as defined above.

Compounds according to formula (1) may be prepared wherein a=0 to 3

$R_1$, $R_2$ and $R_3$ are independently selected from hydrogen and methyl, $R_4$ is hydrogen or $C_1$-$C_4$ alkyl $R_3$ and $R_4$ taken together with the carbon atom and nitrogen atom to which they are respectively attached form a heterocyclic ring selected from pyrrolidinyl and piperidinyl, $R_5$ is hydrogen or (aminomethyl)carbonyl, and $R_6$ is selected from hydrogen, halogen, $C_1$-$C_4$ alkoxy, trifluoromethyl, $C_1$-$C_4$ alkyl and combinations thereof, by the process of (a) reacting a compound of the formula (3)

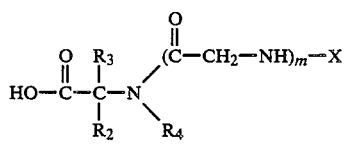
(3)

wherein $R_2$, $R_3$ and $R_4$ are as defined above, m is 0 or 1, and

X is a urethane protecting group, with an amine of the formula (2)

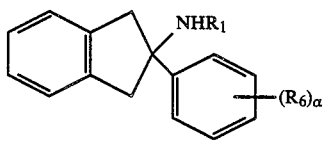
(2)

wherein $R_1$, $R_6$ and a are as defined above, in an inert solvent in the presence of a coupling reagent to provide a compound of the formula (4)

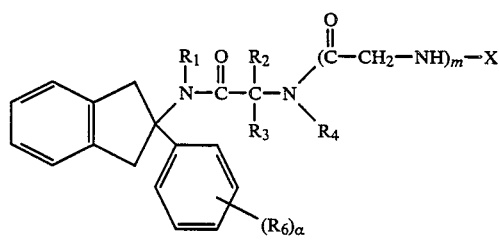
(4)

wherein $R_1$, $R_2$, $R_3$, $R_4$, $R_6$, a, m and X are as defined above; and (b) removing the protecting group X from the product of step (a).

Compounds according to formula (1) may be prepared wherein a=0 to 3

$R_1$ is methyl or hydrogen, $R_2$ and $R_3$ are independently selected from hydrogen and methyl, $R_4$ is selected from hydrogen and $C_1$-$C_4$ alkyl, $R_5$ is selected from hydrogen, $C_1$-$C_4$ alkyl and cyclopropyl, or $R_4$ and $R_5$ taken together with the nitrogen atom to which they are attached form a heterocyclic ring selected from pyrrolidinyl, piperidinyl and morpholinyl, and $R_6$ is selected from hydrogen, halogen, $C_1$-$C_4$ alkoxy, trifluoromethyl, $C_1$-$C_4$ alkyl and combinations thereof, by the process of (a) reacting an amine of the formula (2)

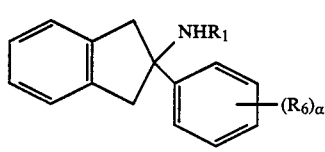
(2)

wherein $R_1$, $R_6$ and a are as defined above, with an activated carboxylic acid derivative which contains a leaving group Y attached to the alpha carbon atom of said derivative in the presence of an acid acceptor to provide a compound of the formula (5)

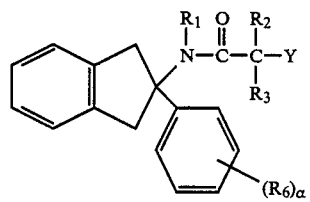
(5)

wherein $R_1$, $R_2$, $R_3$, $R_6$ and a are as defined above, and Y is selected from chloride, bromide, iodide, tosylate and mesylate; and (b) reacting the product of step (a) with ammonia or an amine of the formula $HN(R_4)R_5$, wherein $R_4$ and $R_5$ are as defined above.

DETAILED DESCRIPTION OF THE INVENTION

The 2-amino-N-(2-phenylindan-2-yl)acetamides of formula (1) are conveniently prepared by suitable amide bond-forming reactions from the corresponding amine intermediates of formula (2):

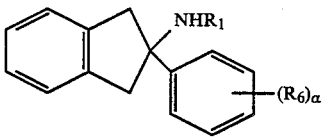
(2)

wherein $R_1$ is methyl or hydrogen; $R_6$ is selected from hydrogen, halogen, $C_1$-$C_4$ alkoxy, trifluoromethyl, $C_1$-$C_4$ alkyl and combinations thereof; and a =0 to 3.

Many amide bond-forming reactions may in principle be utilized for the conversion of the amine intermediate of formula (2) to the amide of formula (1). Two procedures which represent preferred methods for this conversion are designated Method A and Method B.

METHOD A

Method A consists of the direct coupling of readily available suitably protected amino acid derivative (3):

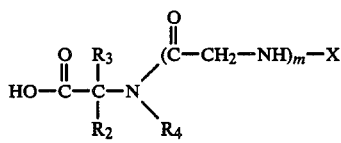

wherein $R_2$, $R_3$ and $R_4$ are as defined above; m is 0 or 1; and X is a urethane protecting group, preferably benzyloxycarbonyl (CBZ) or t-butoxycarbonyl (BOC); with an amine of formula (2), in an inert solvent in the presence of a coupling reagent such as dicyclohexylcarbodiimide (DCC) to provide the coupled products of formula (4):

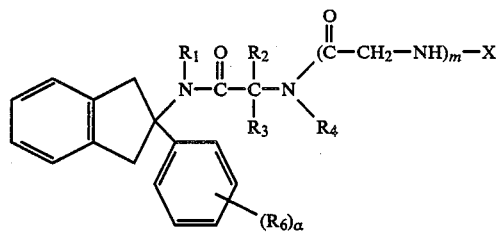

wherein $R_1$, $R_2$, $R_3$, $R_4$, $R_6$, a, m and X are as defined above. The protecting group X is then readily removed by either catalytic hydrogenation (for the CBZ group) or treatment with an acid such as hydrochloric acid (for the BOC group) to provide the corresponding compounds of formula (1) wherein $R_1$, $R_2$, $R_3$, $R_4$ and a are as described above and $R_5$ is hydrogen or (aminomethyl)carbonyl. This procedure is especially useful for the preparation of compounds of formula (1) wherein $R_4$ and $R_5$ are both hydrogen.

By "urethane protecting group" is meant a protecting group X which, together with nitrogen atom to which it is attached, forms a urethane structure, namely >N—COOR, wherein R may be readily removed followed by decarboxylation to provide the corresponding amine.

By "inert solvent" is meant a non-protic solvent such as, for example, methylene chloride, chloroform, ethyl acetate or tetrahydrofuran.

By "coupling reagent" is meant a reagent used to generate an amide bond between the carboxyl group of the amino acid derivative (3) and the amine of formula (2). Suitable coupling agents for this purpose include, for example, DCC, 2-chloro-1-methylpyridinium iodide and diphenylphosophoryl azide.

METHOD B

Method B consists of reacting an amine (2) with an activated carboxylic acid derivative which contains a leaving group attached to the carbon atom alpha to the carbonyl group, e.g. chloroacetyl chloride, in the presence of an acid acceptor, i.e., a tertiary amine such as triethylamine, pyridine, N,N-dimethylaniline, and the like.

By "activated carboxylic acid derivative" is meant an acid derivative which is capable of acylating an amine. Such acid derivatives include, for example, acid chlorides and acid bromides, hydroxysuccinimide ester, p-nitro-phenyl ester, and the like. The activated carboxylic acid derivatives used in the instant process contain an appropriate leaving group Y attached to the carbon atom alpha to the carbonyl group, i.e., a group which may be displaced by the nitrogen of an amine. Such leaving groups include, for example, chloride, bromide, iodide, tosylate, mesylate, and the like.

The reaction of the amine (2) and the activated carboxylic acid derivative produces the corresponding 2-substituted acetamide derivative (5)

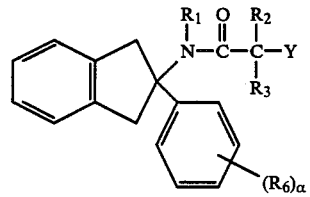

wherein $R_1$, $R_2$, $R_3$, $R_6$, Y and a are as defined above. Compounds of formula (5) may be directly reacted with ammonia, or with amines such as $C_1$-$C_4$ monoalkylamines, $C_2$-$C_8$ dialkylamines, cyclopropylamine, pyrrolidine, piperidine and morpholine, in a solvent such as a lower alkanol (e.g., methanol or ethanol, or a chlorinated solvent (e.g., chloroform or methylene chloride or mixtures thereof). The reaction provides the corresponding 2-amino-N-(2-phenyl-indan-2-yl) acetamides (1) wherein $R_1$, $R_2$, $R_3$, $R_6$ and a are as defined above; $R_4$ is hydrogen or $C_1$-$C_4$ alkyl; $R_5$ is hydrogen, $C_1$-$C_4$ alkyl or cyclopropyl; or $R_4$ and $R_5$ taken together with the nitrogen to which they are attached form a heterocyclic ring taken to be pyrrolidinyl, piperidinyl or morpholinyl.

The intermediate amines (2) are not known. They may be prepared by following Scheme 1, below. Accordingly, an alpha,alpha'-dihalo-ortho-xylene (6), wherein Z is bromine or chlorine, is reacted with a phenylacetonitrile (7), wherein $R_6$ is as defined above, to provide the 2,3-dihydro-2-aryl-1H-indene-2-carbonitrile (8). This reaction may be achieved using sodium amide as a base in ether solvent as reported by F. H. Case, *J. Am. Chem. Soc.*, 56. 715-717 (1934) and C. H. Tilford, M. G. Van Campen, Jr., and R. S. Shelton, *J. Am. Chem. Soc.*, 69, 2902-2906 (1947). Alternatively, the alkylation reaction may be achieved more conveniently under phase transfer conditions in a two-phase mixture of aqueous sodium hydroxide and an organic solvent, e.g. methylene chloride. A quaternary ammonium salt, for example benzyltriethylammonium chloride, may be employed as the phase transfer catalyst.

Scheme 1
Preparation of Amine Intermediates (2)

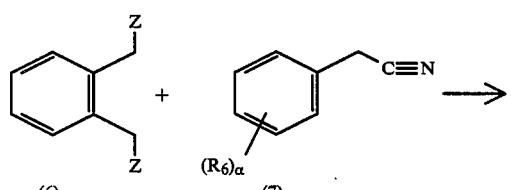

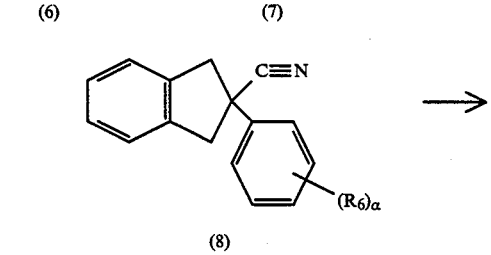

-continued
Scheme 1
Preparation of Amine Intermediates (2)

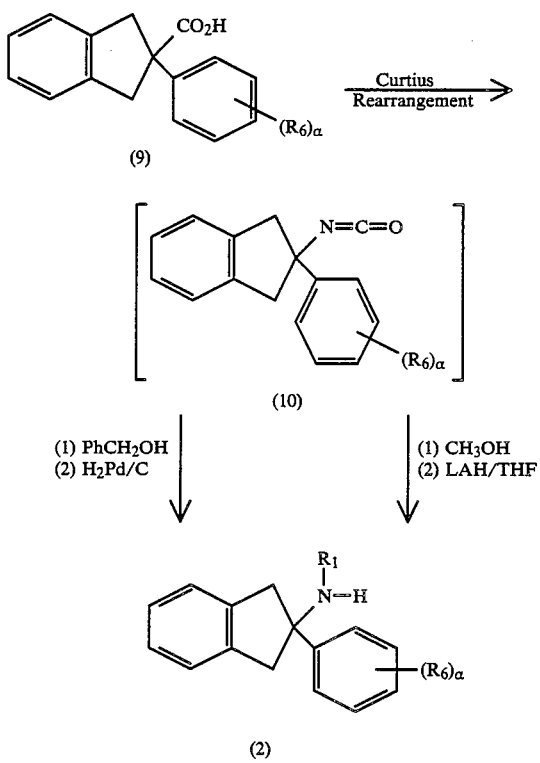

The nitrile (8) is then hydrolyzed to the corresponding 2,3-dihydro-2-aryl-1H-indene-2-carboxylic acid (9) with an inorganic base, e.g , potassium hydroxide, in a mixture of water and ethylene glycol as the solvent. The carboxylic acid (9) is converted to the corresponding isocyanate (10) by a Curtius rearrangement This may be achieved by standard methods (See P. A. S. Smith, Organic Reactions, 3, 337 (1946)). Alternatively and preferably, the carboxylic acid (9) is reacted with diphenylphosphoryl azide in an inert solvent, e.g., benzene or tetrahydrofuran, in the presence of an organic base, e.g., triethylamine (See K. Ninomiya, T. Shiori and S. Yamada, Tet. Lett., 30, 2151–2157 (1974) for the use of diphenylphosphoryl azide in the Curtius rearrangement).

The isocyanate (10) is then reacted with benzyl alcohol to provide the corresponding N-carbobenzoxyurethane. The latter is subjected to catalytic hydrogenation over a palladium catalyst to provide the amine (2) wherein $R_1$ is hydrogen and $R_6$ is as defined above.

Alternatively, the isocyanate (10) is reacted with methanol to provide the corresponding N-carbomethoxy-2,3- dihydro-2-aryl-1H-inden-2-amine, which is reduced with a suitable reducing agent, e.g., lithium aluminum hydride, in an appropriate solvent, e.g., tetrahydrofuran to provide the amine intermediate (2) wherein $R_1$ is methyl and $R_6$ is as defined above.

The 2-amino-N-(2-phenylindan-2-yl)acetamides (1) may possess an asymmetric center. Thus optical isomers are possible. Optical isomers are conveniently prepared from the amine intermediates (2) and optically active amino acid intermediates (3), by the methods described above.

Synthesis of intermediates is illustrated in more detail in the following non-limiting preparation examples

PREPARATION 1

2.3-Dihydro-2-phenyl-1H-indene-2-carbontrile

To a stirred two phase solution of dichloromethane (1 L) and 15% NaOH (750 mL) were added alpha, alpha,-di-bromo-o-xylene (100 g, 0.38 mol), benzyl cyanide (44.3 g, 0.38 mol) and benzyltriethylammonium chloride (17.2 g, 0.075 mol). The two phase solution was vigorously stirred at ambient temperature for 48 hours, at which time benzyl cyanide (20 g, 0.17 mol), benzyltriethylammonium chloride (9.0 g, 0.039 mol), and 15% NaOH (300 mL) were added. The mixture was stirred for an additional 48 hours. The reaction was poured into water (1 L) and extracted with ether (2.5 L). The organic solution was washed with water (3×1 L), brine (500 mL), dried over magnesium sulfate and the solvents evaporated. Vacuum distillation of the residue gave 42.6 g of 2,3-dihydro-2-phenyl-1H-indene- 2-carbontrile, bp 166°–168° C. (5 mm), Lit. bp 160°–180° C. (1 mm), as a colorless oil.

PREPARATION 2

2.3-Dihydro-2-phenyl-1H-indene-2-carboxylic acid

To a stirred mixture of 2,3-dihydro-2-phenyl-1H-indene-2-carbonitrile (10.12 g, 0.0462 mol) in ethylene glycol (80 mL) was added a solution of potassium hydroxide (10.1 g, 0.18 mol) in water (25 mL). The mixture was heated to 110.C under a nitrogen atmosphere for 20 hours. The reaction was cooled to ambient temperature, poured into water (200 mL), acidified with conc. hydrochloric acid (50 mL), and extracted with ethyl acetate (3×100 mL). The combined organic extracts were washed with water (100 mL), brine (100 mL), and dried over magnesium sulfate. The solvent was evaporated to provide 13.6 g of a white solid. Recrystallization from ethyl acetate (75 mL) and hexane (75 mL), and vacuum drying at 65° C. for 3 days, provided 9.5 g of 2,3-dihydro-2-phenyl-1H-indene-2-carboxylic acid, mp 193°–195° C., Lit. mp 194°–195° C.

PREPARATION 3

2.3-Dihydro-2-phenyl-1H-inden-2-amine hydrochloride

To a stirred solution of 2,3-dihydro-2-phenyl-1H-indene-2-carboxylic acid (15.9 g, 0.0668 mol) in benzene (500 mL) were added triethylamine (10.3 mL, 0.0736 mol) and diphenylphosphoryl azide (16.6 mL, 0.0736 mol). The solution was heated to reflux under a nitrogen atmosphere for 3 hours. Benzyl alcohol (27.5 mL, 0.267 mol) was added and the reaction mixture was refluxed for an additional 18 hours. The reaction was cooled to ambient temperature, diluted with ethyl acetate (500 mL), washed with 1N hydrochloric acid (2×150 mL), 5% NaOH (2×75 mL), brine (75 mL), and dried over magnesium sulfate. The solvents were evaporated to provide 42.7 g of a yellow oil. This oil was dissolved in methanol (350 mL) and 2N hydrochloric acid (75 mL) and hydrogenated at 30–40 psi over 10% palladium on carbon (3.5 g) in a Parr apparatus for 2 hours. The catalyst was removed by filtration, the solvents evaporated, and the residue dissolved in chloroform (200 mL) and 2N sodium carbonate (200 mL). The aqueous phase was extracted with chloroform (200 mL). The combined chloroform extracts were washed with brine (100 mL) and dried over magnesium sulfate.

The solvent was evaporated to provide 14.5 g of a colorless oil. This oil was dissolved in methanol (50 mL) and 2-propanol (150 mL) and acidified with HCl gas. The solid which formed was collected by filtration, vacuum dried at 80 C for 2 days to provide 11.5 g of 2,3-dihydro-2-phenyl-1H-inden-2-amine hydrochloride, mp 279–280.C.

PREPARATION 4

2-Chloro-N-(2,3-dihydro-2-phenyl-1H-inden-2-yl)acetamide

To a stirred solution of 2,3-dihydro-2-phenyl-1H-inden-2-amine (23.3 g, 0.111 mol) in dichloromethane (270 mL) at 4° C. under nitrogen were added triethylamine (30.9 mL, 0.222 mol) and then a solution of chloroacetyl chloride (13.5 mL, 0.166 mol) in dichloromethane (100 mL) over a 1 hour period. The reaction was warmed to ambient temperature and stirred at that temperature for 18 hours The reaction mixture was poured into water and extracted with chloroform (2×250 mL). The combined organic extracts were washed with brine (150 mL), dried over magnesium sulfate, and the solvents were evaporated to provide 30.0 g of a dark solid. This solid was triturated with hot cyclohexane (1000 mL). The solvent was decanted and decolorized with carbon. The solid which formed on cooling was isolated by filtration to provide 15.8 g of 2-chloro-N(2,3-dihydro-2-phenyl-1H-inden-2-yl)acetamide, mp 136°–138° C. An analytically pure sample, mp 136°–138° C., was prepared by recrystallization from cyclohexane and ethanol.

PREPARATION 5

N-Methyl-2,3-dihydro-2-phenyl-1H-inden-2-amine maleate

To a stirred solution of 2,3-dihydro-2-phenyl-1H-inden-2-carboxylic acid (15.0 g, 0.063 mol) in benzene (600 mL) were added triethylamine (9.6 mL, 0.069 mol) and diphenylphosphoryl azide (19.0 g, 0.069 mol). The solution was heated to reflux for 2 hours. Methanol (51 mL, 1.3 mol) was added and the solution was refluxed an additional 24 hours. The reaction mixture was cooled to ambient temperature, diluted with ethyl acetate (250 mL), and washed with IN hydrochloric acid (3×250 mL), 5% sodium hydroxide (3×250 mL) and brine (400 mL). The mixture was dried over magnesium sulfate and the solvents evaporated. Th=residual solid was recrystallized from ethyl acetate (40 mL) and hexane (150 mL) to provide 11.7 g N-carbo-methoxy-2,3-dihydro-2-phenyl-1H-inden-2-amine, mp 107°–109° C.

To a stirred suspension of lithium aluminum hydride (5.7 g, 0.15 mol) in tetrahydrofuran (320 mL) at 10° C. under a nitrogen atmosphere was added dropwise a solution of N-carbomethoxy-2,3-dihydro-2-phenyl-1H-inden-2-amine (15.5 g, 0.058 mol) in tetrahydrofuran (150 mL). The mixture was cooled in an ice-water bath and water (5.7 mL), 15% sodium hydroxide (5.7 mL) and water (17 mL) were carefully added. The precipitated solids were removed by filtration, and the filtrate was dried over magnesium sulfate. Removal of solvent gave 12.6 g of an oil. A portion of this oil (1.0 g, 0.0055 mol) was dissolved in ethyl acetate (15 mL), and the resulting solution was added to a solution of maleic acid (0.57 g, 0.0049 mol) in hot ethyl acetate (15 mL). The solid which formed was isolated by filtration and vacuum dried at 55° C. for 60 hours to provide 1.34 g of N-methyl-2,3-dihydro-2-phenyl-1H-inden-2-amine maleate, mp 143°–145° C.

PREPARATION 6

2-Chloro-N-methyl-N-(2,3-dihydro-2-phenyl-1H-inden-2yl)acetamide

By procedures, essentially the same as those described in Preparation 4, and by substitution of N-methyl-2,3-dihydro-2-phenyl-1H-inden-2-amine for 2,3-dihydro-2-phenyl-1H-inden-2-amine, the corresponding 2-chloro-N-methyl-N-(2,3-dihydro-2-phenyl-1H-inden-2-yl)acetamide, mp 134°–137° C. (methanol-cyclohexane), was prepared.

The present invention will be illustrated in more detail by reference to the following non-limiting examples for preparing 2-amino-N-(2-phenylindan-2-yl)acetamides (1).

EXAMPLE 1

2-Amino-N-(2,3-dihydro-2-phenyl-1H-inden-2-yl)acetamide (METHOD A)

To a stirred solution of 2,3-dihydro-2-phenyl-1H-inden-2-amine (10.2 g, 0.049 mol) in chloroform (200 mL) were added N-CBZ-glycine (10.8 g. 0.052 mol) and then a solution of dicyclohexylcarbodiimide (11.1 g, 0.053 mol) in chloroform (70 mL). The mixture was stirred for 18 hours at ambient temperature. The mixture was filtered and the solvent was evaporated. The residue was dissolved in ethyl acetate (200 mL) and filtered again. The filtrate was washed with 1N hydrochloric acid (2×100 mL), 2N sodium carbonate (2×100 mL), brine (100 mL) and dried over magnesium sulfate. The solvent was then evaporated. The residue was recrystallized from ethyl acetate (75 mL) and cyclohexane (150 mL) to provide 17.1 g of 2-[(carbobenzoxy)amino]-N-(2,3-dihydro-2-phenyl-1H-inden-2-yl)acetamide, mp 63°–70° C. To a solution of the latter (14.3 g, 0.037 mol) in methanol (200 mL), tetrahydrofuran (75 mL) and IN hydrochloric acid (70 mL), was added 10% palladium on carbon (1.4 g). The mixture was shaken on a Parr apparatus for 1.5 hours. The catalyst was removed by filtration, the solvents evaporated and the residue dissolved in chloroform (200 mL) and 2N sodium carbonate (200 mL). The aqueous layer was extracted with chloroform (2×100 mL). The combined chloroform extracts were washed with brine (100 mL), dried over magnesium sulfate, and the solvent evaporated. The residue was dissolved in methanol (50 mL) and 2-propanol (75 mL) and acidified with HCl gas. The solid which formed was collected by filtration and vacuum dried at 80° C. for 3 days to provide 7.3 g of 2-amino-N-(2,3-dihydro-2-phenyl-1H-inden-2-yl)acetamide, mp 275°–276° C.

EXAMPLE 2

N-(2,3-Dihydro-2-phenyl-1H-inden-2-yl)-2-(propylamino)-acetamide hydrochloride (METHOD B)

To a stirred solution of 2-chloro-N-(2,3-dihydro-2-phenyl-1H-inden-2-yl)acetamide (8.0 g, 0.028 mol) in methanol (165 mL) and chloroform (65 mL) was added n-propylamine (9.2 mL, 0.112 mol) and the mixture was stirred at ambient temperature under nitrogen for 2 days. An additional portion of n-propylamine (5.0 mL, 0.061 mol) was added and the reaction mixture was stirred for an additional 2 days at 36° C. The solvents were evaporated, the residue was dissolved in chloroform (250 mL) and 5% NaOH (300 mL) and the phases were separated. The aqueous phase was extracted with chloroform (2×200 mL). The combined chloroform extracts were washed with brine (100 mL), dried over magnesium sulfate, and the solvent evaporated. The residue was dissolved in ethyl acetate (400 mL) and methanol (75 mL) and acidified with a saturated solution of hydrogen chloride in 2-propanol. The solid obtained by filtration was recrystallized from ethanol (225 mL), and vacuum dried at 80° C. for 2 days to provide 6.24 g of N (-2,3-dihydro-2-phenyl-1H-inden-2-yl)-2-(propylamino)acetamide hydrochloride, mp 259°–261° C.

EXAMPLE 3

N-(2,3-Dihydro-2-phenyl-1H-inden-2-yl)-2-[(1-methylethyl)-amino]acetamide hydrochloride By procedures essentially the same as those described in Example 2, and by substituting isopropylamine for n-propylamine, the corresponding N-(2,3-dihydro-2-phenyl-1H-inden-2-yl)-2-[(1-methylethyl)amino]acetamide hydrochloride, mp 267°–269° C. (ethanol), was prepared.

EXAMPLE 4

2-(Cyclopropylamino)-N-(2,3-dihydro-2-phenyl-1H-inden-2-yl)acetamide hydrochloride By procedures essentially the same as those described in Example 2, and by substituting cyclopropylamine for n-propylamine, the corresponding 2-(cyclopropylamino)-N-(2,3-dihydro-2-phenyl-1H-inden-2-yl)acetamide hydrochloride, mp 230°–231° C. (ethanol), was prepared.

EXAMPLE 5

(S)-2-Amino-N-(2,3-dihydro-2-phenyl-1H-inden-2-yl)propanamide maleate

By procedures essentially the same as those described in Example and by substituting N-CBZ-L-alanine for N-CBZ-glycine, the corresponding (S)-2-amino-N-(2,3-dihydro-2-phenyl-1H-inden-2-yl)propanamide maleate, mp 110°–112° C. (methanol, ethyl acetate, ether), was prepared.

EXAMPLE 6

(R)-2-Amino-N-(2.3-dihydro-2-phenyl-1H-inden-2-yl)propanamide fumarate

By procedures essentially the same as those described in Example 1, and by substituting N-CBZ-D-alanine for N-CBZ-glycine, the corresponding (R)-2-amino-N-(2,3-dihydro-2-phenyl-1H-inden-2-yl)propanamide fumarate, mp 209°–210° C. (methanol), was prepared.

EXAMPLE 7

2[[(Aminomethyl)carbonyl]amino]-N-(2,3-dihydro-2-phenyl-1H-inden-2-yl)acetamide fumarate By procedures essentially the same as those described in Example 1, and by substituting N-CBZ-glycylglycine, for N-CBZ-glycine the corresponding 2-[[(aminomethyl)carbonyl]amino]-N-(2,3-dihydro-2-phenyl-1H-inden-2yl)acetamide fumarate, mp 180°–182° C. (2-propanol), was prepared.

EXAMPLE 8

N-(2,3-Dihydro-2-phenyl-1H-inden-2-yl)-N-methyl-2-(dimethylamino)acetamide hydrochloride To a stirred solution of dimethylamine (30 mL, 0.45 mol) in methanol (150 mL) at 0° C. under nitrogen were added 2-chloro-N-methyl-N-(2,3-dihydro-2-phenyl-1H-inden-2-yl)acetamide (8.0 g, 0.027 mol) and chloroform (110 mL). The mixture was stirred at ambient temperature for 60 hours. The solvents were evaporated, the residue was dissolved in chloroform (250 mL) and 5% NaOH (250 mL), and the phases were separated. The aqueous phase was extracted with chloroform (3×200 mL). The combined chloroform extracts were washed with brine (200 mL), dried over magnesium sulfate and the solvent evaporated. The residual solid (8.1 g) was dissolved in ethanol (175 mL) and acidified with HCl gas. The solid which formed was collected by filtration and vacuum dried at 65° C. for 48 hours to provide 8.0 g of N-(2,3-dihydro-2-phenyl-1H-inden-2-yl)-N-methyl-2(dimethylamino)acetamide, mp 244°–245° C.

EXAMPLE 9

(S)-N-(2,3-Dihydro-2-phenyl-1H-inden-2-yl)-2-pyrrolidinecarboxamide hydrochloride By procedures essentially the same as those described in Example 1, and by substituting N-CBZ-L-proline for N-CBZ-glycine, the corresponding (S)-N-(2,3-dihydro-2-phenyl-1H-inden-2-yl)-2-pyrrolidinecarboxamide hydrochloride, mp 278°–279° C. (methanol, ethyl acetate), was prepared.

EXAMPLE 10

N-(2.3-Dihydro-2-phenyl-1H-inden-2-yl)-2-(dimethylamino)acetamide hydrochloride

By procedures essentially the same as those described in Example 2, and by substituting dimethylamine for n-propylamine, the corresponding N-(2,3-dihydro-2-phenyl-1H-inden-2-yl)-2-(dimethylamino)acetamide hydrochloride, mp 235°–237° C. (ethyl acetate, methanol), was prepared.

EXAMPLE 11

2-Amino-N-(2.3-dihydro-2-phenyl-1H-inden-2-yl)-N-methylacetamide hydrochloride

A stirred suspension of 2-chloro-N-methyl-N-(2,3-dihydro-2-phenyl-1H-inden-2-yl)acetamide (10.0 g, 0.0334 mol) in absolute ethanol (280 mL) was saturated with ammonia gas at ambient temperature. The solution was heated to 78°–85° C. in a steel bomb for 48 hours. The reaction was cooled to ambient temperature and the solvent was evaporated. The residue was dissolved in chloroform (200 mL) and 5% NaOH (200 mL), the phases separated, and the aqueous phase extracted with chloroform (2×200 mL). The combined chloroform extracts were washed with brine (200 mL), dried over magnesium sulfate and the solvent evaporated. The residual oil was purified by silica gel chromatography on a Waters Prep 500, eluting with ammoniated 5% methanol-chloroform to provide 6.51 g of a yellow solid. This solid was dissolved in ethyl acetate (100 mL) and 2-propanol (35 mL) and acidified with HCl gas. The solid which formed was isolated by filtration and vacuum dried at 80 C for 65 hours to provide 3.60 g of 2-amino-N(2,3-dihydro-2-phenyl-1H-inden-2-yl)-N-methylacetamide hydrochloride, mp 218°–219° C.

EXAMPLE 12

N-(2,3-Dihydro-2-phenyl-1H-inden-2-yl)-N-methyl-2-(methylamino)acetamide hydrochloride By procedures essentially the same as those described in Example 8, and by substituting monomethylamine for dimethylamine, the corresponding N-(2,3-dihydro-2-phenyl-1H-inden-2-yl)-N-methyl-2-(methylamino)acetamide hydrochloride, mp 220°–221° C. (2-propanol, ethyl acetate), was prepared.

EXAMPLE 13

N-(2,3-Dihydro-2-phenyl-1H-inden-2-yl)-2-piperidinecarboxamide hydrochloride

By procedures essentially the same as those described in Example 1, and by substituting N-CBZ-DL-pipecolinic acid for N-CBZ-glycine, the corresponding N-(2,3-dihydro-2-phenyl-1H-inden-2-yl)-2-piperidinecarboxamide hydrochloride, mp 298°–300° C. (methanol, ethyl acetate), was prepared.

EXAMPLE 14

2-Amino-N-(2,3-dihydro-2-phenyl-1H-inden-2-yl)-2-methylpropanamide hydrochloride By procedures essentially the same as those described in Example 1, and by substituting N-CBZ-2-methylalanine for N-CBZ-glycine, the corresponding 2-amino-N-(2,3-dihydro-2-phenyl-1H-inden-2-yl)-2-methylpropanamide hydrochloride, mp 148°–150° C. (methanol, 2-propanol), was prepared.

EXAMPLE 15

N-(2,3-Dihydro-2-phenyl-1H-inden-2-yl)-2-(methylamino)acetamide hydrochloride

By procedures essentially the same as those described in Example 2, and by substituting monomethylamine for n-propylamine, the corresponding N-(2,3-dihydro-2-phenyl-1H-inden-2-yl)-2-(methylamino)acetamide, mp 276°–77° C. (ethanol), was prepared.

EXAMPLE 16

2-(Butylamino)-N-(2,3-dihydro-2-phenyl-1H-inden-2-yl)acetamide hydrochloride

By procedures essentially the same as those described in Example 2, and by substituting n-butylamine for n-propylamine, the corresponding 2-(butylamino)-N-(2,3-dihydro-2-phenyl-1H-inden-2-yl) acetamide hydrochloride, mp 270°–271° C. (ethanol), was prepared.

EXAMPLE 17

N-(2,3-Dihydro-2-phenyl-1H-inden-2-yl)-2-(1-pyrrolidinyl)acetamide hydrochloride By procedures essentially the same as those described in Example 2, and by substituting pyrrolidine for n-propylamine, the corresponding N-(2,3-dihydro-2-phenyl-1H-inden-2-yl)-2-(1-pyrrolidinyl)acetamide hydrochloride, mp 222°–223° C. (2-propanol, ethyl acetate), was prepared.

EXAMPLE 18

N-(2,3-Dihydro-2-phenyl-1H-inden-2-yl)-2-(1-piperidinyl)acetamide

By procedures essentially the same as those described in Example 2, and by substituting piperidine for n-propylamine, the corresponding N-(2,3-dihydro-2-phenyl-1H-inden-2-yl)-2-(1-piperidinyl)acetamide may be prepared.

EXAMPLE 19

N-(2,3-Dihydro-2-phenyl-1H-inden-2-yl)-2-(4-morpholinyl)acetamide

By procedures essentially the same as those described in Example 2, and by substituting morpholine for n-propylamine, the corresponding N-(2,3-dihydro-2-phenyl-1H-inden-2-yl)-2-(4-morpholinyl)acetamide may be prepared.

Application of the methodology described above will provide all the compounds of the invention including, for example, the following compounds: 2-amino-N-[2,3-dihydro-2(2-bromophenyl)-1H-inden-2-yl]acetamide hydrochloride; 2-amino-N-[2,3-dihydro-2-(4-chlorophenyl)-1H-inden-2-yl]acetamide hydrochloride; 2-amino-N-[2,3-dihydro-2-(3-methylphenyl)-1H-inden-2-yl]acetamide hydrochloride; 2-amino-N-[2,3-dihydro-2-[4-(trifluoromethyl)phenyl]-1H-inden-2-yl]acetamide hydrochloride; 2-amino-N-[2,3-dihydro-2-(3-fluorophenyl)-1H-inden-2-yl]acetamide hydrochloride; 2-amino-N-[2,3-dihydro-2-(4-methoxyphenyl)-1H-inden-2-yl]acetamide hydrochloride; 2-amino-N-[2,3-dihydro-2-(3,4-dimethoxyphenyl)-1H-inden-2-yl]acetamide hydrochloride; 2-amino-N-[2,3-dihydro-2-(2,4-difluorophenyl)-1H-inden-2-yl]acetamide hydrochloride; 2-(methyl-amino)-N-[2,3-dihydro-2-(4-n-butoxyphenyl)-1H-inden-2yl]acetamide hydrochloride; 2-(dimethylamino)-N-[2,3-dihydro-2-(4-n-butylphenyl)-1H-inden-2-yl]acetamide hydrochloride.

The compounds of the invention are basic and thus can form salts with pharmaceutically acceptable acid addition salts. Salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

The compounds of the invention possess useful pharmaceutical properties. In particular, they are useful antiepileptic agents. Some of the compounds possess antihypoxia activity. Antiepileptic activity was measured by recording a test compound's ability to prevent maximal electroshock-induced seizures (MES) in mice following oral or intraperitoneal administration of the compound. Activities in the range of 10–400 mg/kg after oral administration were observed.

Antihypoxia activity was measured by recording a test compound,s ability to protect mice from death due to oxygen deprivation in an environmental chamber flushed with an atmosphere of 96% nitrogen and 4% oxygen. Some of the compounds of formula (1) had minimum active doses in the range of 3–50 mg/kg and 100%S's (the dose which produced a 100% increase in survival time) in the range of 25–50 mg/kg after intravenous dosing.

For pharmaceutical purposes, the compounds of this invention can be administered to warm-blooded animals perorally or parenterally as active ingredients in customary dosage unit compositions. These compositions consist essentially of a dosage unit form containing the active ingredient and at least one inert pharmaceutical carrier. Dosage unit forms contemplated by the present invention include tablets, capsules, solutions, suspensions, lozenges, coated pills and parenteral compositions such as intramuscular, intravenous or intradermal preparations. Sustained release dosage forms are also contemplated where the active ingredient is bound to an ion exchange resin which, optionally, can be coated with a diffusion barrier coating to modify the release properties of the resin.

The quantity of active ingredient administered in such dosage forms can vary over a wide range depending upon the mode of administration, the size and weight of the patient, and whether the nature of the treatment is prophylactic or therapeutic in nature. In general, dosage unit forms contain from about 5 mg to about 100 mg of the active ingredient and in man the dose is administered from 1 to about 4 times daily. The total daily dosage will be from about 5 mg to about 500 mg, although lower and higher amounts can be used. A preferred total daily dose would be from about 10 mg to about 100 mg of active ingredient.

Pharmaceutical carriers or excipients used in the preparation of pharmaceutical compositions may be either organic or inorganic, solid or liquid in nature. Suitable solid excipients include gelatin, microcrystalline cellulose, lactose, starches and magnesium stearate. Suitable liquid excipients include water and alcohols such as ethanol, benzylalcohol and polyethylene glycols. In general, the preferred liquid excipients particularly useful for injectable preparations include water, saline solution, dextrose solution and glycol solutions such as aqueous propylene glycol or aqueous polyethylene glycol. The properties of the formulations may be enhanced by the addition of one or more adjuvants possessing properties as viscosity enhancers, surfactants, pH modifiers, preservatives, sweeteners, stability enhancers, coloring agents, suspending agents, granulating agents, coating agents, disintegration modifiers, propellants, emulsifying agents and humectants.

The present invention may be embodied in other specific forms without departing from the spirit or essential attributes thereof and, accordingly, reference should be made to the appended claims, rather than to the foregoing specifications, as indicating the scope of the invention.

We claim:

1. A compound having the formula:

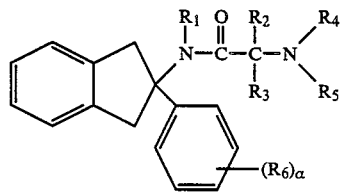

or pharmaceutically acceptable acid addition salts thereof, including such compounds and salts thereof in the form of their enantiomers, or mixtures of their enantiomers, a=0 to 3, $R_1$, $R_2$ and $R_3$ are independently selected from hydrogen and methyl, $R_4$ is hydrogen, or $C_1$-$C_4$ alkyl, $R_5$ is selected from hydrogen, or $C_1$-$C_4$ alkyl, cyclopropyl and (aminomethyl)carbonyl, or $R_4$ and $R_5$ taken together with the nitrogen atom to which they are attached from a heterocyclic ring selected from pyrrolidinyl, piperidinyl and morpholinyl, or $R_3$ and $R_4$ taken together with the carbon atom and nitrogen atom to which they are respectively attached form a heterocyclic ring selected from pyrrolidinyl and piperidinyl, and $R_6$ is selected from hydrogen, halogen, $C_1$-$C_4$ alkoxy, trifluoromethyl, $C_1$-$C_4$ alkyl and combinations thereof.

2. A compound according to claim 1 wherein the compound is 2-amino-N-(2,3-dihydro-2-phenyl-1H-inden-2yl)acetamide, or pharmaceutically acceptable acid addition salts thereof.

3. A compound according to claim 1 wherein the compound is N-(2,3-dihydro-2-phenyl-1H-inden-2-yl)-2(propylamino)acetamide, or pharmaceutically acceptable acid addition salts thereof.

4. A compound according to claim 1 wherein the compound is N-(2,3-dihydro-2-phenyl-1H-inden-2-yl)-2-[(1methylethyl)amino]acetamide, or pharmaceutically acceptable acid addition salts thereof.

5. A compound according to claim 1 wherein the compound is 2-(cyclopropylamino)-N-(2,3-dihydro-2-phenyl-1H-inden-2-yl)acetamide, or pharmaceutically acceptable acid addition salts thereof.

6. A compound according to claim 1 wherein the compound is (S)-2-amino-N-(2,3-dihydro-2-phenyl-1H-inden-2yl)propanamide, or pharmaceutically acceptable acid addition salts thereof.

7. A compound according to claim 1 wherein the compound is (R)-2-amino-N-(2,3-dihydro-2-phenyl-1H-inden-2yl)propanamide, or pharmaceutically acceptable acid addition salts thereof.

8. A compound according to claim 1 wherein the compound is 2-[[(aminomethyl)carbonyl]amino]-N-(2,3-dihydro-2-phenyl-1H-inden-2-yl)acetamide, or pharmaceutically acceptable acid addition salts thereof.

9. A compound according to claim 1 wherein the compound is N-(2,3-dihydro-2-phenyl-1H-inden-2-yl)-N-methyl-2-(dimethylamino)acetamide, or pharmaceutically acceptable acid addition salts thereof.

10. A compound according to claim 1 wherein the compound is (S)-N-(2,3-dihydro-2-phenyl-1H-inden-2-yl)-2-pyrrolidinecarboxamide or pharmaceutically acceptable acid addition salts thereof.

11. A compound according to claim wherein the compound is N-(2,3-dihydro-2-phenyl-1H-inden-2-yl)-2(dimethylamino)acetamide, or pharmaceutically acceptable acid addition salts thereof.

12. A compound according to claim 1 wherein the compound is 2-amino-N-(2,3-dihydro-2-phenyl-1H-inden-2-yl)-N-methylacetamide, or pharmaceutically acceptable acid addition salts thereof.

13. A compound according to claim 1 wherein the compound is N-(2,3-dihydro-2-phenyl-1H-inden-2-yl)-N-methyl-2-(methylamino)acetamide, or pharmaceutically acceptable acid addition salts thereof.

14. A compound according to claim 1 wherein the compound is N-(2,3-dihydro-2-phenyl-1H-inden-2-yl)-2piperidinecarboxamide, or pharmaceutically acceptable acid addition salts thereof.

15. A compound according to claim 1 wherein the compound is 2-amino-N-(2,3-dihydro-2-phenyl-1H-inden-2-yl)-2-methylpropanamide, or pharmaceutically acceptable acid addition salts thereof.

16. A compound according to claim 1 wherein the compound is N-(2,3-dihydro-2-phenyl-1H-inden-2-yl)-2-(methylamino)acetamide, or pharmaceutically acceptable acid addition salts thereof.

17. A compound according to claim 1 wherein the compound is 2-(butylamino)-N-(2,3-dihydro-2-phenyl- 1H-inden-2-yl)acetamide, or pharmaceutically acceptable acid addition salts thereof.

18. A compound according to claim 1 wherein the compound is N-(2,3-dihydro-2-phenyl-1H-inden-2-yl)-2-(1pyrrolidinyl)acetamide, or pharmaceutically acceptable acid addition salts thereof.

19. A compound according to claim 1 wherein the compound is N-(2,3-dihydro-2-phenyl-1H-inden-2-yl)-2-(1piperidinyl)acetamide, or pharmaceutically acceptable acid addition salts thereof.

20. A compound according to claim 1 wherein the compound is N-(2,3-dihydro-2-phenyl-1H-inden-2-yl)-2-(4morpholinyl)acetamide, or pharmaceutically acceptable acid addition salts thereof.

21. A method of treating a warm-blooded animal for epilepsy comprising administering to such animal an effective amount of a compound according to claim 1.

* * * * *

UNITED STATES PATENT AND TRADEMARK OFFICE
CERTIFICATE OF CORRECTION

PATENT NO. : 4,873,241

DATED : October 10, 1989

INVENTOR(S) : James J. Napier et al.

It is certified that error appears in the above-identified patent and that said Letters Patent is hereby corrected as shown below:

On the title page, ABSTRACT, 9th line after formula: change "from" to --form--;
Column 9, line 49: change "Th=" to --The--;
Column 11, line 13: change "N(-2,3" to --N-(2,3--;
Column 11, line 44: after "Example" insert --1,--;
Column 11, line 67: change "inden-2yl" to --inden-2-yl--;
Column 12, line 22: change "2(dimethyl" to --2-dimethyl--;
Column 14, line 16: change "2(2-bromophenyl)" to --2-(2-bromophenyl)--; Claim 1, 4th line after the formula: after "enantiomers," insert --wherein--; Column 2, line 34 and claim 1, 12th line after formula: change "from" to --form--; Claim 2, line 3: change "inden-2yl)" to --inden-2-yl)--; Claim 11, line 1: after "claim" insert --1--;
Claim 11, line 3: change "2(dimethylamino)" to --2-(dimethylamino)--; Claim 14, line 3: change "2 piperidinecarboxamide" to --2-piperidinecarboxamide--.

Signed and Sealed this

Twenty-fifth Day of December, 1990

Attest:

HARRY F. MANBECK, JR.

*Attesting Officer*  *Commissioner of Patents and Trademarks*